United States Patent [19]

Grohe

[11] Patent Number: 4,914,228

[45] Date of Patent: Apr. 3, 1990

[54] PREPARATION OF HALOGENATED QUINOLONECARBOXYLIC ACIDS

[75] Inventor: Klaus Grohe, Odenthal, Fed. Rep. of Germany

[73] Assignee: Bayer Aktiengesellschaft, Leverkusen, Fed. Rep. of Germany

[21] Appl. No.: 209,751

[22] Filed: Jun. 21, 1988

Related U.S. Application Data

[62] Division of Ser. No. 29,939, Mar. 24, 1987, Pat. No. 4,782,156, which is a division of Ser. No. 754,563, Jul. 12, 1985, Pat. No. 4,680,401.

[30] Foreign Application Priority Data

Jul. 18, 1984 [DE] Fed. Rep. of Germany ....... 3426483

[51] Int. Cl.$^4$ .............................................. C07C 69/78
[52] U.S. Cl. ..................................................... 560/103
[58] Field of Search ......................................... 560/103

[56] References Cited

U.S. PATENT DOCUMENTS

| | | | |
|---|---|---|---|
| 2,726,947 | 12/1955 | Baumgartner | 560/103 X |
| 3,047,574 | 7/1962 | Kalm | 544/172 X |
| 4,309,566 | 1/1982 | Konz et al. | 560/103 X |
| 4,386,035 | 5/1983 | Maurer et al. | 560/103 X |
| 4,680,401 | 7/1987 | Grohe | 546/153 |

FOREIGN PATENT DOCUMENTS 0077501  4/1983  European Pat. Off. ............. 560/103

Primary Examiner—Joseph Paul Brust
Attorney, Agent, or Firm—Sprung Horn Kramer & Woods

[57] ABSTRACT

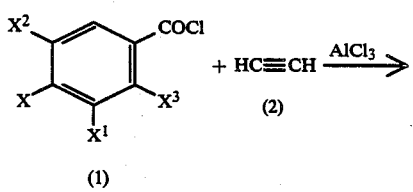

(1)

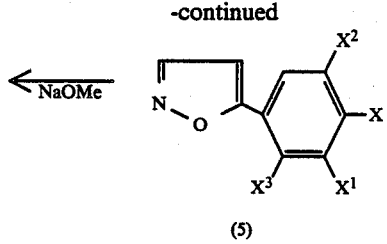

(5)

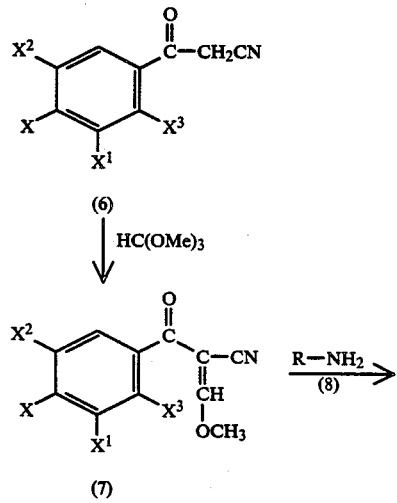

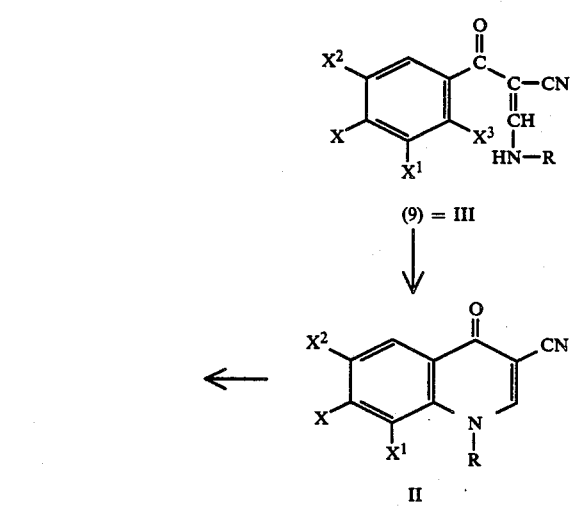

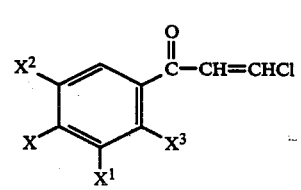

(3)

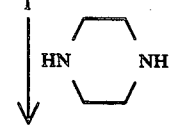

(4)

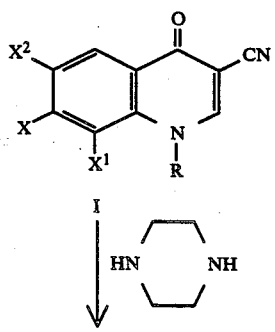

(Abstract continued on next page.)

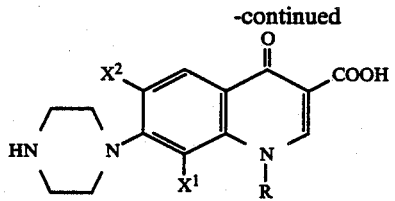
The end products are known bacterials. Several of the intermediates are new.
1 Claim, No Drawings

PREPARATION OF HALOGENATED QUINOLONECARBOXYLIC ACIDS

This is a division of application Ser. No. 029,939, filed Mar. 24, 1987, now U.S. Pat. No. 4,782,156, which is a divisional of Ser. No. 754,563, filed July 12, 1985, now U.S. Pat. No. 4,680,401.

The present invention relates to a process for the preparation of halogenated quinolonecarboxylic acids, which are useful intermediates for the synthesis of highly active antibacterial medicaments.

It has been found that the halogenated quinolonecarboxylic acids of the formula I

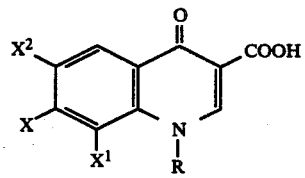

I in which
R denotes alkyl with 1–3 carbon atoms, 2-fluoroethyl, phenyl, methoxy or cyclopropyl,
X denotes halogen, preferably chlorine or fluorine,
$X^1$ denotes hydrogen or halogen, preferably fluorine, and
$X^2$ denotes hydrogen or halogen, preferably fluorine, are obtained by a process in which the corresponding 2-benzoyl-3-amino-acrylonitriles of the formula III

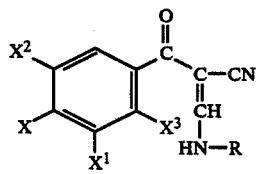

III in which

R, X, $X^1$ and $X^2$ have the abovementioned meaning and
$X^3$ represents halogen, in particular chlorine or fluorine,
are subjected to a cyclocondensation reaction and the quinolonecarboxylic acid nitriles thereby formed, of the formula II

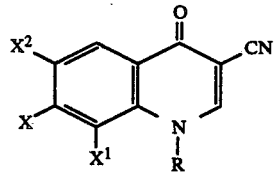

II are hydrolyzed.

The cyclocondensation mentioned is advantageously carried out using sodium alcoholates or potassium alcoholates with 1–4 C atoms in the alcohol part, for example Na methylate, or sodium hydride or, particularly preferably, sodium carbonate or potassium carbonate.

The hydrolysis can be carried out in an alkaline or acid medium.

The quinolonecarboxylic acid nitriles used as starting substances are prepared as follows:

The halogenated benzoyl halides (1) are used in the presence of anhydrous aluminum chloride to acylate acetylene (2) to give the chlorovinyl ketones (3), which are cyclized with hydroxylamine (4) to give the isoxazoles (5). With an alkali metal alcoholate, these are converted, via ring-opening, into the desired benzoylacetonitriles (6). The reaction of (6) with trimethyl o-formate leads to the 2-benzoyl-3-methoxy-acrylonitriles (7), which react with primary amines (8) to give the 2-benzoyl-3-amino-acrylonitriles (9)=III. The cyclocondensation of (9) to give the quinolonecarboxylic acid nitriles II is carried out, for example, with potassium carbonate in dimethylformamide at 150° C.

According to the invention, hydrolysis of the quinolonecarboxylic acid nitriles II thus obtained then leads to the carboxylic acids I.

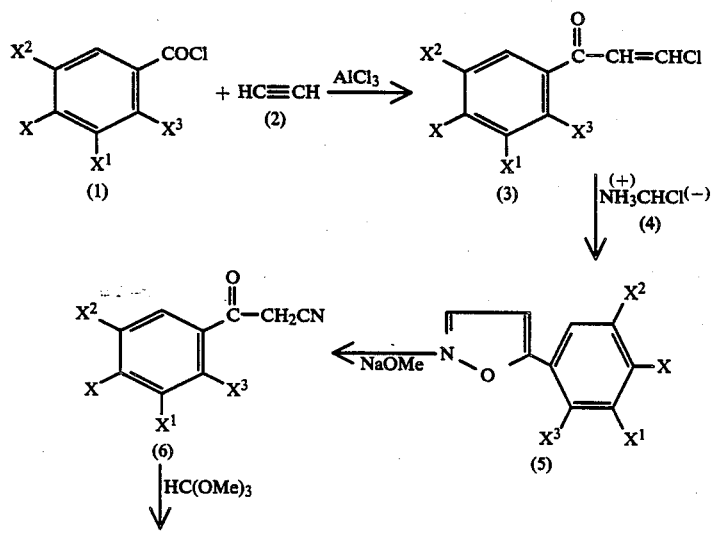

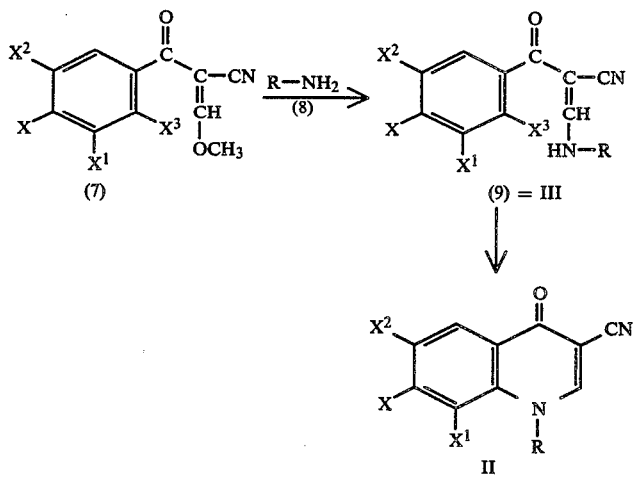

In these formulae, $X^3$ represents halogen, preferably chlorine or fluorine.

The benzoylacetonitriles (6) can also be obtained in another manner, for example by reacting benzoic acid esters (10) with acetonitrile in the presence of a base, such as, for example, sodium hydride or K tert.-butanolate.

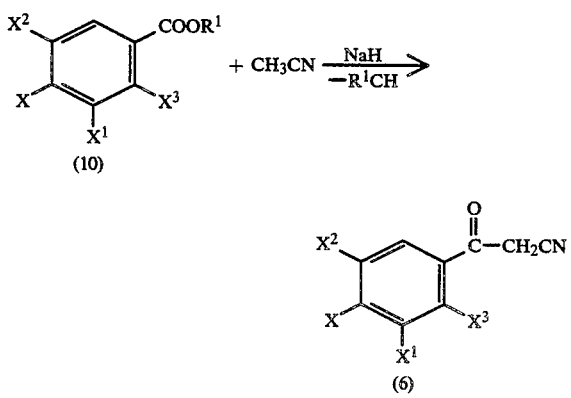

In this equation, $R^1$ denotes an alkyl radical with 1 to 4 carbon atoms, preferably methyl or ethyl.

The benzoyl chlorides (1) are known, for example from DE-OS (German Published Specification) 3,142,856, or they can be prepared in the customary manner from the known carboxylic acids with thionyl chloride. The benzoic acid esters (10) are obtained from the corresponding carboxylic acids or carboxylic acid chlorides and the corresponding alcohols.

Examples of the benzoyl chlorides (1) which may be mentioned are: 2,4-dichloro-5-fluoro-benzoyl chloride, 2,4,5-trifluorobenzoyl chloride, 2,3,4,5-tetrafluorobenzoyl chloride, 2,4,5-trichlorobenzoyl chloride, 2,3,4,5-tetrachlorobenzoyl chloride and 2,4,5-trifluoro-3-chloro-benzoyl chloride.

It has already been disclosed that halogenated benzoyl chlorides can be converted into quinolanecarboxylic acid esters and quinolonecarboxylic acids via the corresponding benzoylmalonic acid esters, benzoylacetic acid esters, 2-benzoyl-3-alkoxyacyl acid esters and 2-benzoyl-3-alkylaminoacrylic acid esters (DE-OS (German Published Specification) 3,142,854).

However, this process has some disadvantages. Thus, selective hydrolysis of the benzoylmalonic acid esters to give the corresponding benzoylacetic acid esters is frequently associated with losses in yield. In addition to the desired benzoylacetic acid esters, varying amounts of acetophenone are obtained.

The halogenated quinolonecarboxylic acids prepared according to the invention can be converted into highly active antibacterial medicaments. Thus, for example, when 7-chloro-1-cyclopropyl-6-fluoro-1,4-dihydro-4-oxo-3-quinolinecarboxylic acid is reacted with piperazine, the known broad band chemotherapeutic ciprofloxacin (DE-OS (German Published Specification) 3,142,854) is formed:

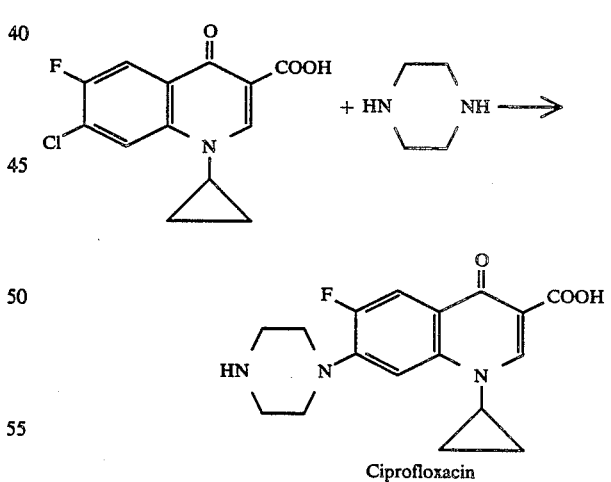

Ciprofloxacin

EXAMPLE 1

I. 2,4-Dichloro-5-fluoro-benzoyl-acetonitrile

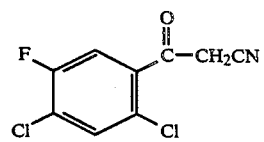

(1) 2-Chlorovinyl 2,4-dichloro-5-fluoro-phenyl ketone 113.75 g (0.5 mole) of 2,4-dichloro-5-fluorobenzoyl chloride are added dropwise to a suspension of 73 g of anhydrous aluminum chloride and 200 ml of dry 1,2-dichloroethane at 0°–10° C., while cooling with ice and stirring. Acetylene is passed in at 40°–50° C. for 6.5 hours. The reaction mixture is poured onto ice, the organic phase is taken up in methylene chloride and the mixture is subsequently extracted with methylene chloride. After drying with sodium sulphate, the solvent is distilled off in vacuo. 121.7 g of 2-chlorovinyl 2,4-dichloro-5-fluoro-phenyl ketone are obtained as a crude product of melting point 65°–70° C. Distillation under a fine vacuum gives 99.8 g (78.7%) of pure product of boiling point: 124°–128° C./0.1 mbar and melting point 71°–73° C.

(2) 5-(2,4-Dichloro-5-fluoro-phenyl)-isoxazole

A mixture of 57.6 g of 2-chlorovinyl 2,4-dichloro-5-fluoro-phenyl ketone, 16.4 g of hydroxylamine hydrochloride and 150 ml of methanol is heated at the boiling point under reflux for 6 hours, a precipitate separating out after about one hour. This is filtered off cold with suction, washed with a little methanol and dried at 50° C. in vacuo. 33.3 g (63.2%) of 5-(2,4-dichloro-5-fluorophenyl)-isoxazole of melting point 112°–113° C., which, according to investigations by NMR spectroscopy, contains about 6 mole % of an isomer, are obtained.

(3) 2,4-Dichloro-5-fluoro-benzoylacetonitrile 23.2 g (0.1 mole) of 5-(2,4-dichloro-5-fluorophenyl)-isoxazole are added in portions to a solution of 2.3 g (0.1 g atom) of sodium in 100 ml of absolute ethanol in the course of about 30 minutes while cooling with ice and stirring. The mixture is then stirred at room temperature for 1 hour, the alcohol is distilled off in vacuo, the residue is dissolved in about 1 liter of warm water, the solution is extracted twice with methylene chloride, the aqueous phase is acidified to pH=4 with 10 percent strength hydrochloric acid (~38 ml) and the precipitate is filtered off cold with suction and dried in vacuo at 50° C. 21.7 g (93%) of 2,4-dichloro-5-fluoro-benzoylacetonitrile of melting point 98°–99° C. are obtained.

Condensation process (a) A mixture of 47.4 g of ethyl 2,4-dichloro-5-fluorobenzoate and 8.2 g of anhydrous acetonitrile are added dropwise to a suspension of 6.1 g of 80% strength sodium hydride in 100 ml of anhydrous tetrahydrofuran under reflux in the course of about 1 hour. The mixture is heated at the boiling point under reflux for a further hour and cooled to room temperature, and 150 ml of ether are added. The precipitate is filtered off with suction and dissolved in 50 ml of ice-water and the solution is acidified to pH=6 with 10% strength hydrochloric acid. The precipitate is filtered off cold with suction, rinsed with ice-water and dried in vacuo at 40° C. 16 g of 2,4-dichloro-5-fluoro-benzoylacetonitrile of melting point 96°–98° C. are obtained.

(b) 22.4 g (0.2 mole) of potassium tert.-butanolate are added in portions to a mixture of 47.4 g (0.2 mole) of ethyl 2,4-dichloro-5-fluoro-benzoate, 8.5 g of anhydrous acetonitrile and 100 ml of absolute tert.-butanol. When the slightly exothermic reaction has subsided, the mixture is refluxed for 4 hours, the solvent is stripped off in vacuo and the residue is taken up in $H_2O/CH_2Cl_2$.

20 ml of glacial acetic acid are added to the aqueous phase, while cooling with ice, and the precipitate is filtered off with suction, washed with water and dried in vacuo at 50° C. 25.7 g (55.4%) of 2,4-dichloro-5-fluoroacetonitrile of melting point 96°–99° C. are obtained.

The ethyl 2,4-dichloro-5-fluoro-benzoate used as the starting material is obtained as follows:

84 g of 2,4-dichloro-5-fluoro-benzoyl chloride are added dropwise to 250 ml of anhydrous ethanol at 50° to 60° C., the temperature being maintained by occasional cooling with ice-water. The mixture is then refluxed for about a further hour, the excess alcohol is distilled off and the residue is fractionated in vacuo. 84.9 g (~97%) of ethyl 2,4-dichloro-5-fluoro-benzoate are obtained at 132°–135° C./8 mbar.

II.
2-(2,4-Dichloro-5-fluoro-benzoyl)-3-methoxyacrylonitrile

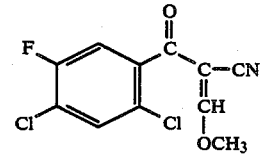

A mixture of 21 g of 2,4-dichloro-5-fluorobenzoylacetonitrile, 19.2 g of methyl o-formate and 23.1 g of acetic anhydride is refluxed at a bath temperature of 150° C. for 3 hours. The volatile constituents are then distilled off under a waterpump vacuum and finally under a fine vacuum at a bath temperature of 120° C. 24.5 g (99%) of 2-(2,4-dichloro-5-fluorobenzoyl)-3-methoxy-acrylonitrile are obtained. A sample recrystallized from toluene gives colorless crystals of melting point 159° C.

III.
2-(2,4-Dichloro-5-fluoro-benzoyl)-3-cyclopropylamino-acrylonitrile

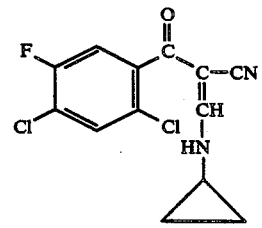

5.6 g of cyclopropylamine are added dropwise to a solution of 22.5 g of 2-(2,4-dichloro-5-fluoro-benzoyl)-3-methoxy-acrylonitrile in 80 ml of ethanol, while cooling with ice and stirring. The mixture is stirred at room temperature for 25 minutes and then heated at the boiling point for 15 minutes. The solvent is removed in vacuo and the residue is recrystallized from ethanol/light petrol. 17.7 g of 2-(2,4-dichloro-5-fluorobenzoyl)-3-cyclopropyl-amino-acrylonitrile of melting point 95° C. are obtained.

IV.
7-Chloro-1-cyclopropyl-6-fluoro-1,4-dihydro-4-oxo-3-quinolinecarboxylic acid nitrile

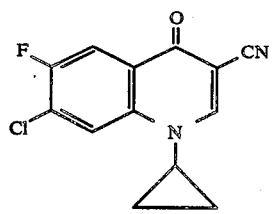

17.7 g of 2-(2,4-dichloro-5-fluoro-benzoyl)-3-cyclopropylamino-acrylonitrile, 9 g of anhydrous potassium carbonate and 60 ml of anhydrous dimethylformamide are heated at 150°–160° C. for 2 hours. The hot mixture is poured onto ice and the precipitate is filtered off with suction and washed thoroughly with water. After drying in vacuo at 100° C., 14.9 g of pure 7-chloro-1-cyclopropyl-6-fluoro-1,4-dihydro-4-oxo-3-quinolinecarboxylic acid nitrile of melting point 239°–241° C. are obtained.

V.
7-Chloro-1-cyclopropyl-6-fluoro-1,4-dihydro-4-oxo-3-quinolinecarboxylic acid 2.6 g (0.01 mole) of 7-chloro-1-cyclopropyl-6-fluoro-1,4-dihydro-4-oxo-3-quinolinecarboxylic acid nitrile are heated at the boiling point under reflux with 12 ml of water and 10 ml of concentrated sulphuric acid for 1.5 hours. The bath temperature here is 170°–180° C. and the internal temperature is 132°–134° C. The mixture is poured into 30 ml of ice-water and the precipitate is filtered off with suction, washed thoroughly with water and dissolved hot in 30 ml of 10 percent strength sodium hydroxide solution. The solution is filtered hot, the residue is rinsed with 100 ml of hot water and the filtrate is cooled with ice and acidified to pH=1 with half-concentrated hydrochloric acid. The light yellow precipitate is filtered off with suction, washed with water and dried at 100° C. in vacuo. Yield: 2.2 g of 7-chloro-1-cyclopropyl-6-fluoro-1,4-dihydro-4-oxo-3-quinolinecarboxylic acid of melting point 234°–236° C. After recrystallization from glycol monomethyl ether, 1.8 g (64.6%) of light yellow crystals of melting point 240°–241° C. are obtained.

EXAMPLE 2
I. 2,4-Dichloro-benzoylacetonitrile

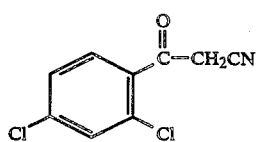

A mixture of 43.8 g of ethyl 2,4-dichloro-benzoate and 8.2 g of anhydrous acetonitrile is added dropwise to a suspension of 6.1 g of 80% strength sodium hydride in 100 ml of anhydrous tetrahydrofuran in the course of about 1 hour under reflux. The mixture is heated at the boiling point under reflux for a further hour and cooled to room temperature and 150 ml of ether are added. The precipitate is filtered off with suction and dissolved in 50 ml of ice-water and the solution is acidified to pH=6 with 10% strength hydrochloric acid. The precipitate is filtered off cold with suction, rinsed with ice-water and dried in vacuo at 40° C. 12 g of 2,4-dichlorobenzoylacetonitrile of melting point 96°–98° C. are obtained.

II. 2-(2,4-Dichloro-benzoyl)-3-methoxyacrylonitrile

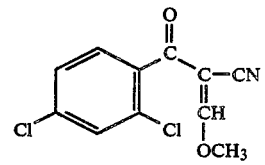

A mixture of 8.8 g of 2,4-dichloro-benzoylacetonitrile, 69.2 g of methyl o-formate and 10.5 g of acetic anhydride is refluxed at a bath temperature of 150° C. for 3 hours. The volatile constituents are then distilled off in vacuo and finally under a fine vacuum at a bath temperature of 120° C. 11 g of 2-(2,4-dichloro-benzoyl)-3-methoxy-acrylonitrile are obtained as a viscous oil.

III.
2-(2,4-Dichloro-benzoyl)-3-cyclopropyl-amino-acrylonitrile

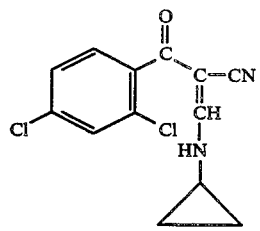

2.5 g of cyclopropylamine are added dropwise to a solution of 11 g of 2-(2,4-dichloro-benzoyl)-3-methoxyacrylonitrile in 40 ml of ethanol, while cooling with ice and stirring. The mixture is stirred at room temperature for 25 minutes and then heated at the boiling point for 15 minutes. The solvent is removed in vacuo and the residue is recrystallized from ethanol/light petrol. 10.5 g of 2-(2,4-dichloro-benzoyl)-3-cyclopropylaminoacrylonitrile of melting point 93°–94° C. are obtained.

IV.
7-Chloro-1-cyclopropyl-1,4-dihydro-4-oxo-3-quinolinecarboxylic acid nitrile

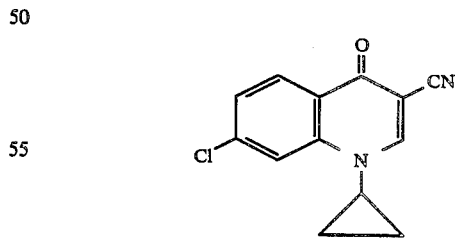

10.2 g of 2-(2,4-dichloro-benzoyl)-3-cyclopropylamino-acrylonitrile, 6.1 g of anhydrous potassium carbonate and 40 ml of anhydrous dimethylformamide are heated at 150°–160° C. for 2 hours. The hot mixture is poured onto ice and the precipitate is filtered off with suction and washed thoroughly with water. After drying in vacuo at 100° C., 8.3 g of crude 7-chloro-1-cyclopropyl-1,4-dihydro-4-oxo-3-quinolinecarboxylic acid nitrile are obtained. After recrystallization from acetonitrile, the light yellow crystals have a melting point of 270°–272° C. Yield: 7 g

V.
7-Chloro-1-cyclopropyl-1,4-dihydro-4-oxo-3-quinolinecarboxylic acid

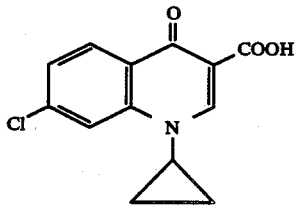

2.5 g (0.01 mole) of 7-chloro-1-cyclopropyl-1,4-dihydro-4-oxo-3-quinolinecarboxylic acid nitrile are heated at the boiling point under reflux with 12 ml of water and 10 ml of concentrated sulphuric acid for 1.5 hours. The bath temperature here is 170°–180° C. and the internal temperature is 132°–134° C. The mixture is poured into 30 ml of ice-water and the precipitate is filtered off with suction, washed thoroughly with water and dissolved hot in 30 ml of 10 percent strength sodium hydroxide solution. The solution is filtered hot, the residue is rinsed with 100 ml of hot water and the filtrate is cooled with ice and acidified to pH=1 with half-concentrated hydrochloric acid. The light yellow precipitate is filtered off with suction, washed with water and dried in vacuo at 100° C. Yield: 2.4 g of 7-chloro-1-cyclopropyl-1,4-dihydro-4-oxo-3-quinoline-carboxylic acid of melting point 307°–308° C.

It will be understood that the specification and examples are illustrative but not limitative of the present invention and that other embodiments within the spirit and scope of the invention will suggest themselves to those skilled in the art.

I claim:
1. Ethyl 2,4-dichloro-5-fluorobenzoate.
* * * * *